Figure 2:
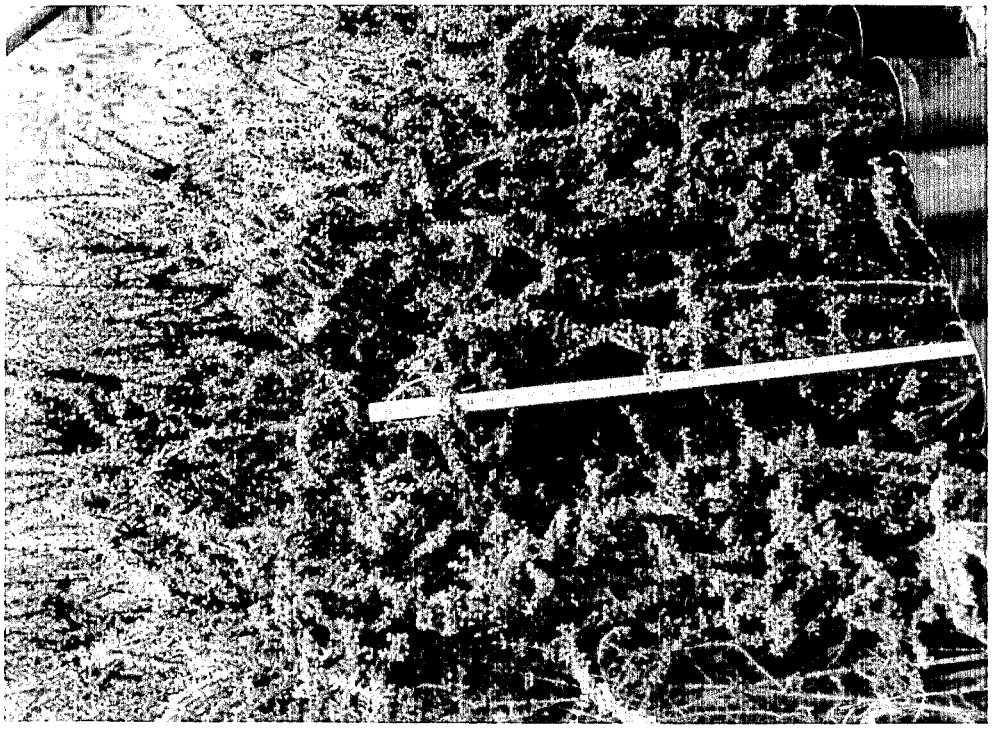
Figure 1:
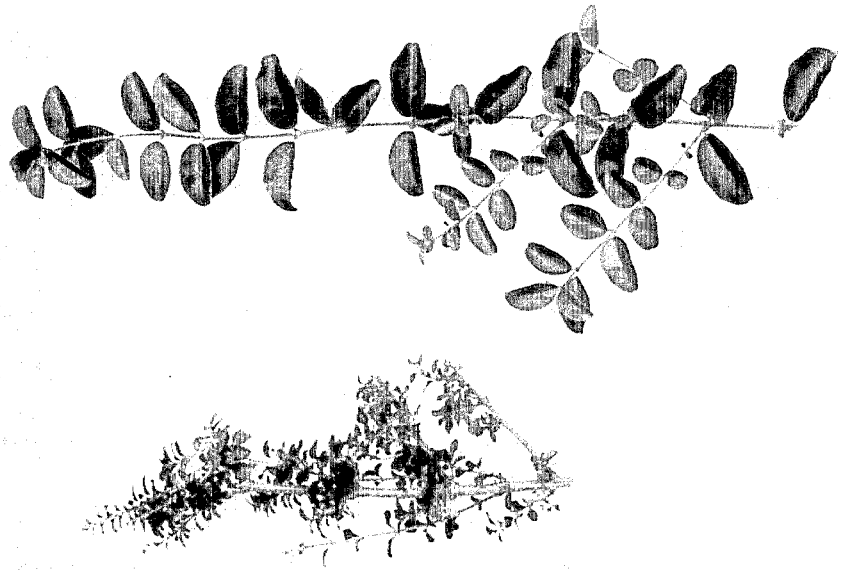
Figure 3:
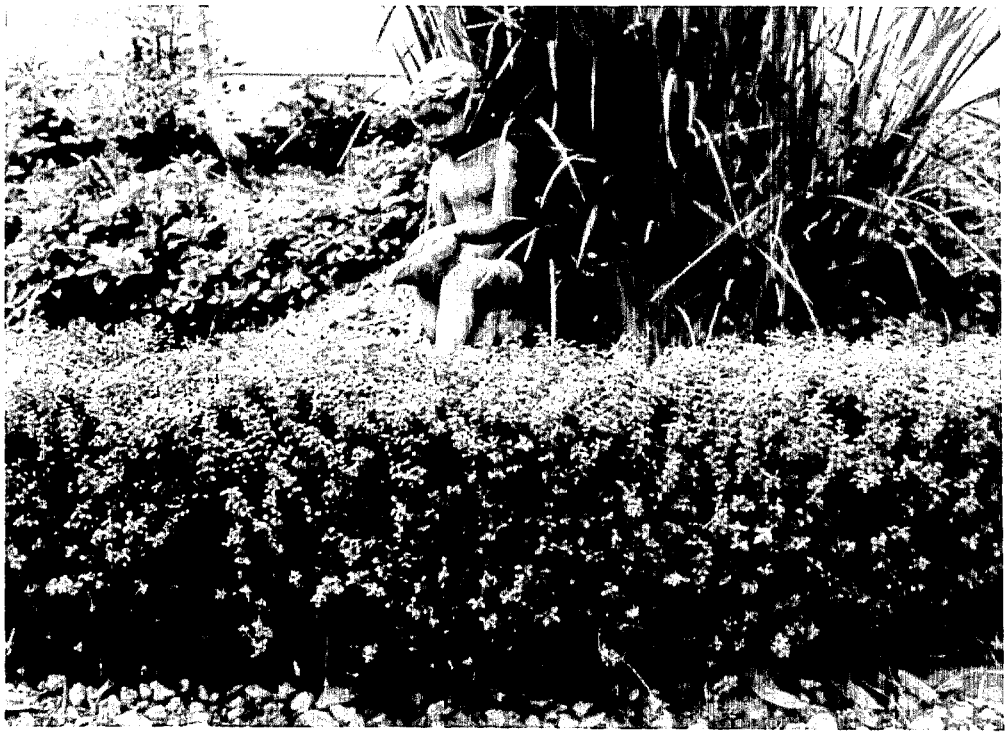

United States Patent [19]

Wates

[11] Patent Number: Plant 5,469

[45] Date of Patent: May 14, 1985

[54] PRIVET PLANT

[76] Inventor: Byron E. Wates, 9403 Mirror Pond Ct., Fairfax, Va. 22031, executrix; E. Inez Wates

[21] Appl. No.: 305,494

[22] Filed: Sep. 25, 1981

[51] Int. Cl.[3] ..... A01H 5/00

[52] U.S. Cl. ..... Plt./54

[58] Field of Search ..... Plt./54

*Primary Examiner*—Robert E. Bagwill

[57] ABSTRACT

A new and distinct variety of Ligustrum distinguished by its small leaves and dense growth habit.

3 Drawing Figures

BACKGROUND OF THE NEW PLANT

This new variety of Ligustrum was found by me as a chance seedling among numerous other seedlings under a Chinese Privet growing in a yard in Alabama. I propagated the plant asexually by stem cuttings and have twelve of these original cuttings which are now nineteen years old. Both these older plants and successive generations have retained the distinctive characteristics.

DESCRIPTION OF THE PHOTOGRAPHS

The accompanying photograph No. 1 shows the Wates Privet (L.) compared to a standard Chinese Privet (R.), photograph No. 2 shows the height to which unpruned cuttings grew in nine years, and photograph No. 3 shows the cuttings used as a miniature edging held to a height and spread of less than 1′ by pruning twice a year.

DESCRIPTION OF THE NEW PLANT

The following is a description of my new Privet plant as observed at my former home and nursery location at 4118 Olley Lane, Fairfax, Va., with color designations according to The R.H.S. Colour Chart published by The Royal Horticultural Society of London, England.

Origin: Chance seedling.

Parentage: Chinese Privet (unpatented).

*Botanic name.*—*Ligustrum sinensis.*

*Common name.*—Chinese Privet.

Growth rate: About 6 to 12 inches per year.

Growth habit:

*Natural.*—Narrow, upright.

*Sheared.*—Dense, 4 inch hedge possible in 2 to 3 years from rooted cuttings.

Branching character: Very twiggy; shearing emphasizes this characteristic.

Foliage: Abundant — leaf nodes about 5 to 8 millimeters apart.

*Leaf.*—Size: Mature leaf — average 8 millimeters long and 5 millimeters wide. Shape: Ovate. Color: Mature leaves — Upper side — Yellow-green 147A. Under side — Yellow-green 146A. Immature leaves — Upper side — Yellow-green 144B. Upper side — Yellow-green 145A. Texture: Smooth. Petiole: About 1 to 3 millimeters long.

My new Privet does not resemble any other ligustrum except in a miniaturized form. Because of its tiny leaves and dense growth, it is particularly suited for use as a dwarf edging for formal gardens or for areas where a small scale plant is desirable. Its appearance and growth habit are novel and distinctive. It has never blossomed.

This new form of Privet plant is evergreen in the Fairfax, Va. area, particularly so if the new growth is sheared late in the summer. In severe winters it defoliates somewhat. This Privet plant has been tested for hardiness as far north as New Hampshire, Connecticut, two locations in Maryland, and one location in the mountain area of Virginia near Woodstock. It has proven completely evergreen in the two Maryland locations and completely hardy in all other test areas, though it completely defoliates in the most northern test areas.

It is claimed:

1. A new and distinctive variety of Ligustrum substantially as herein shown and described, particularly characterized by its small leaves, dense foliage and twiggy growth habit.

* * * * *